US008755879B2

(12) United States Patent
Hang et al.

(10) Patent No.: US 8,755,879 B2
(45) Date of Patent: Jun. 17, 2014

(54) SLEEP TRACKING AND WAKING OPTIMIZATION SYSTEM AND METHOD THEREFOR

(71) Applicant: Forty Winks, LLC, St. Louis, MO (US)

(72) Inventors: Zimin Hang, Rockville, MD (US); James Nolan Tin Ahad, Arcadia, CA (US); Xiaoyang Ye, St. Louis, MO (US); Daniel Alexander Corin, St. Louis, MO (US)

(73) Assignee: Forty Winks, LLC, St. Louis, MO (US)

( * ) Notice: Subject to any disclaimer, the term of this patent is extended or adjusted under 35 U.S.C. 154(b) by 0 days.

(21) Appl. No.: 14/050,944

(22) Filed: Oct. 10, 2013

(65) Prior Publication Data
US 2014/0107520 A1 Apr. 17, 2014

Related U.S. Application Data

(60) Provisional application No. 61/795,191, filed on Oct. 12, 2012.

(51) Int. Cl.
*A61B 5/0476* (2006.01)
(52) U.S. Cl.
CPC ..................................... *A61B 5/0476* (2013.01)
USPC ........................................................ 600/545
(58) Field of Classification Search
CPC ... A61B 5/0476; A61B 5/04012; G08B 21/06
USPC .................. 600/544, 545; 340/575
See application file for complete search history.

(56) References Cited

U.S. PATENT DOCUMENTS

| 4,736,751 A | 4/1988 | Gevins et al. |
|---|---|---|
| 6,468,234 B1 | 10/2002 | Van der Loos |
| 8,096,960 B2 | 1/2012 | Loree, IV et al. |
| 8,437,843 B1 | 5/2013 | Kayyali et al. |
| 2002/0007124 A1 | 1/2002 | Woodward |
| 2005/0107722 A1 | 5/2005 | Ozaki et al. |

(Continued)

FOREIGN PATENT DOCUMENTS

| WO | 2005028029 A2 | 3/2005 |
|---|---|---|
| WO | 2012153263 A1 | 11/2012 |

OTHER PUBLICATIONS

Guerrero-Mora et al., "Sleep-wake Detection Based on Respiratory Signal Acquired Through a Pressure Bed Sensor," 34th Annual International Conference of the IEEE EMBS, San Diego, CA, Aug. 28-Sep. 1, 2012.

*Primary Examiner* — Navin Natnithithadha
*Assistant Examiner* — Etsub Berhanu
(74) *Attorney, Agent, or Firm* — The Marbury Law Group, PLLC

(57) ABSTRACT

Analog electrical and pressure data obtained by an EEG/pressure sensor matrix from the subject are sent to a signal processing module that derives digital EEG data from the electrical signal and pressure data without using sensors attached to a subject's head. The pressure data are used as a secondary signal to measure the physical orientation of the subject's head. The physical orientation is used to transform the derived EEG signal to a known coordinate axis (the orientation of the subject's head) to obtain useful, consistent, and accurate EEG data. The EEG may be used to determine a sleep state of a subject and to awaken the subject while in a particular state.

29 Claims, 12 Drawing Sheets

(56) References Cited

U.S. PATENT DOCUMENTS

| | | |
|---|---|---|
| 2006/0152378 A1 | 7/2006 | Lokhorst et al. |
| 2006/0293608 A1* | 12/2006 | Rothman et al. .............. 600/545 |
| 2008/0191885 A1* | 8/2008 | Loree, IV et al. ............. 340/575 |
| 2011/0112442 A1 | 5/2011 | Meger et al. |
| 2011/0178377 A1 | 7/2011 | Heneghan et al. |
| 2011/0295083 A1 | 12/2011 | Doelling et al. |
| 2012/0029322 A1* | 2/2012 | Wartena et al. ............... 600/301 |
| 2012/0265054 A1 | 10/2012 | Olson |
| 2013/0023740 A1 | 1/2013 | Kirchner et al. |
| 2013/0035541 A1 | 2/2013 | Kashima et al. |

* cited by examiner

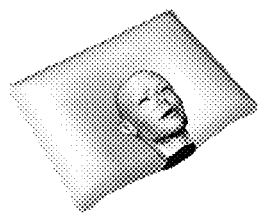 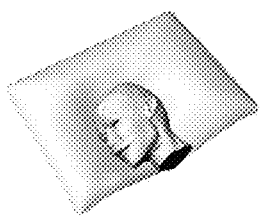 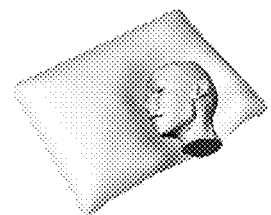
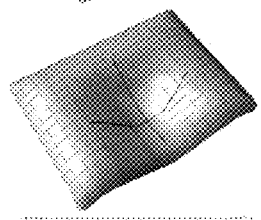 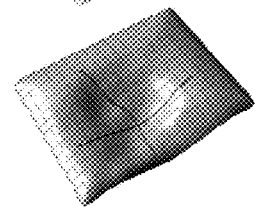 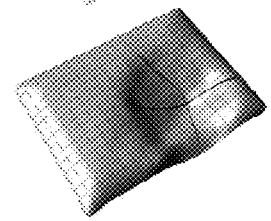
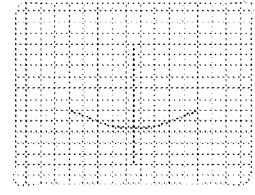 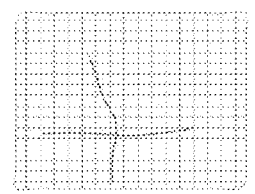 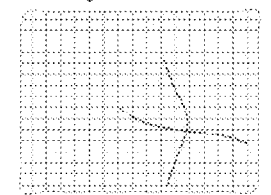
FIG 3A  FIG 3B  FIG 3C

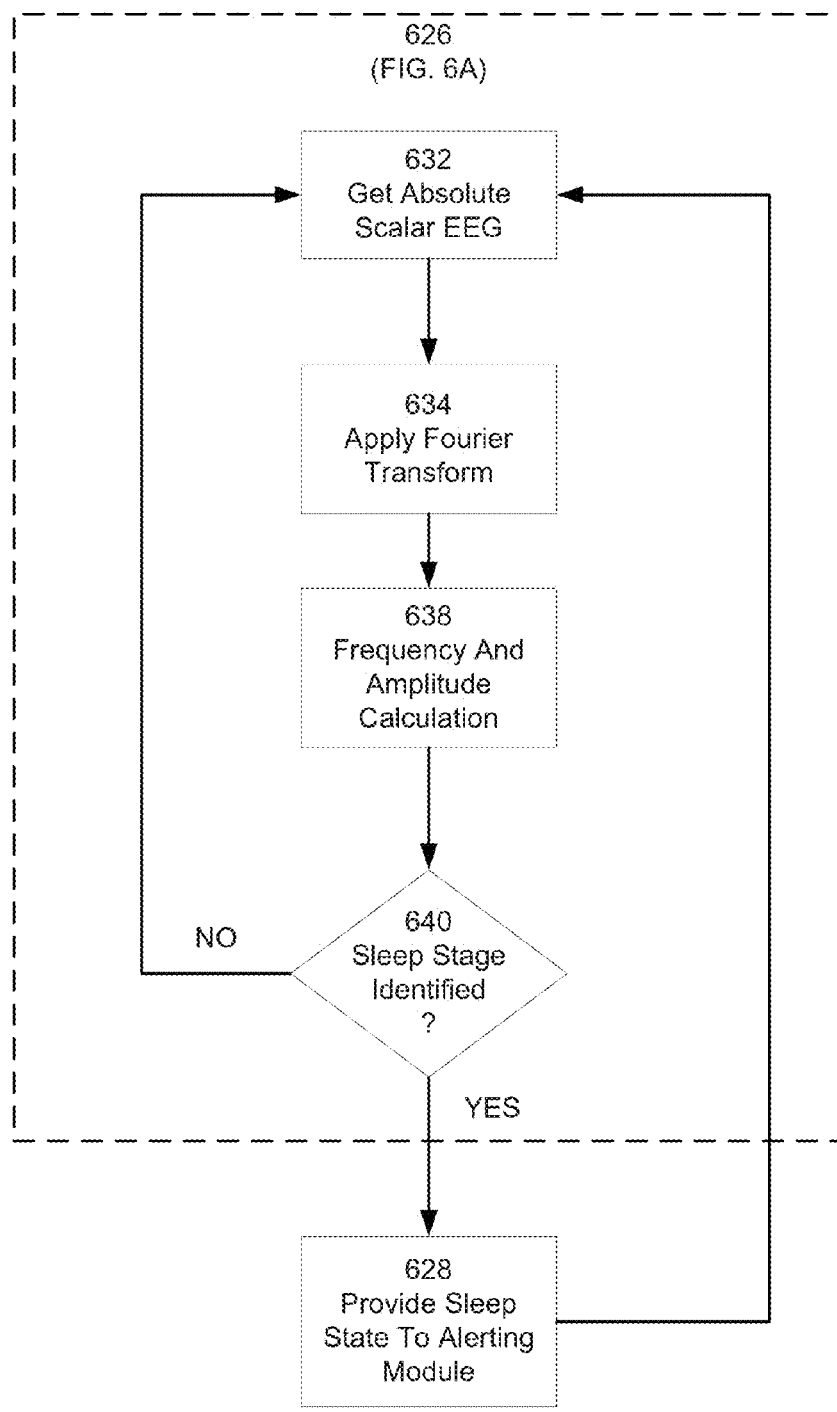

SLEEP TRACKING AND WAKING OPTIMIZATION SYSTEM AND METHOD THEREFOR

CROSS REFERENCE TO RELATED APPLICATIONS

This application claims the benefit of Provisional Application No. 61/795,191 filed Oct. 12, 2012. The 61/795,191 application is incorporated by reference herein, in its entirety, for all purposes.

BACKGROUND

In recent times, sleep has become a research topic of great interest. Sleep is a universal animal behavior that has significant import in modern human development and productivity. As a result, there is great motivation to study sleep, its benefits and the benefits that may be derived from optimizing sleep on an individual basis.

Electroencephalography (EEG) has been used pervasively in sleep research as a data collection tool due to its advantages in the field. Firstly, EEG creates reliable and reproducible quantitative results in a field that was, previously, largely qualitative. Secondly, it does so non-invasively by measuring electric signals at the scalp. Finally, during sleep, EEG signals have properties and behaviors that are largely invariant among varied populations. From EEG data, researchers have been able to accurately typify sleep stage cycles from EEG signals alone.

Sleep is known to be an episodic process with various stages, starting from a light state of sleep to a deeper state and back to the light state. When awoken during a light state of sleep, post-waking fatigue and sleep inertia (e.g. the desire to return to a sleeping state while waking) are reduced in physiologically healthy patients. Sleep stages can be typified by brainwave patterns and brainwaves during light sleep are similar to brainwaves while awake. The theta waves (4-7 Hz) that occupy most of Stage 1 and 2 sleep are significantly more analogous to the alpha waves (8-12 Hz) that dominate our awake state than the delta waves (0.5-2 Hz) of deep sleep. Most neural state changes (ex. being asleep to being awake) require some period of time for neurochemical and metabolic elements to direct the change; going from a state of light sleep to an awake state is faster than going from a state of deep sleep to an awake state. Because the transition from light sleep to an awake state is rapid, the duration of sleep inertia and fatigue should be minimized, as light state brainwave patterns are the most analogous to those observed in the awake state.

SUMMARY

Embodiments herein are directed to detecting the sleep state of a human subject and waking the subject when in a light sleep state in order to reduce morning fatigue and improve restfulness.

In an embodiment, analog electrical and pressure data obtained by an EEG/pressure sensor matrix from the subject are sent to a signal processing module that derives digital EEG data from the electrical signal and pressure data without using sensors attached to a subject's head. The pressure data are used as a secondary signal to measure the physical orientation of the subject's head. The physical orientation is used to transform the derived EEG signal to a known coordinate axis (the orientation of the subject's head) to obtain useful, consistent, and accurate EEG data.

In an embodiment, a system for acquiring an EEG signal suitable for use in electroencephalography from a subject includes a sensor matrix and processing control unit.

The sensor matrix includes a plurality of EEG electrodes configured to receive electrical signals from the brain of the subject and a plurality of pressure sensors configured to receive pressure signals indicative of the placement of the head of the subject on the sensor matrix. The processing control unit is configured to perform operations that include obtaining EEG electrode data from the electrical signals received by the sensor matrix, determining a scalar EEG voltage for each EEG electrode, obtaining pressure data from the pressure signals received by the sensor matrix, determining a pressure normal unit vector for each EEG electrode from the pressure data, summing the product of the pressure normal unit vector and the scalar EEG voltage for each EEG electrode to obtain a relative mean EEG vector, and obtaining a scalar absolute EEG signal from a dot product of a unit orientation vector and the relative mean EEG vector. In an embodiment, the unit orientation vector is obtained by determining points of maximum pressure along orthogonal axes using the pressure data, deriving rotation and axial tilt of the subject's head from attributes of the points of maximum pressure, producing the unit orientation vector from the angles of the rotation and axial tilt.

In an embodiment, the sensor matrix may be a flexible sheet that is a component of a pillow configured for receiving the head of the subject.

In another embodiment, the sensor matrix and the processing control unit may be used in conjunction with a memory and an alerting device to awaken a subject. The memory receives the EEG electrode data derived from the electrical signals and receives pressure data derived from the pressure signal. The processing control unit determines a sleep state of the subject from the EEG vector and issues a command to power on the alerting device to awaken the subject while the subject is in or is approaching a light sleep state. In an embodiment, the operations performed by the processing control unit are performed by a computing device selected from the group consisting of a laptop computer, a desktop computer, a portable computing device, a tablet or a smart phone.

DESCRIPTION OF THE DRAWINGS

FIGS. 3A, 3B and 3C graphical representations illustrating pressure distributions from three orientations of the head of a subject according to an embodiment.

FIG. 6B is a flow diagram illustrating a process by which a sleep state is identified according to an embodiment.

DETAILED DESCRIPTION

Figure 1:
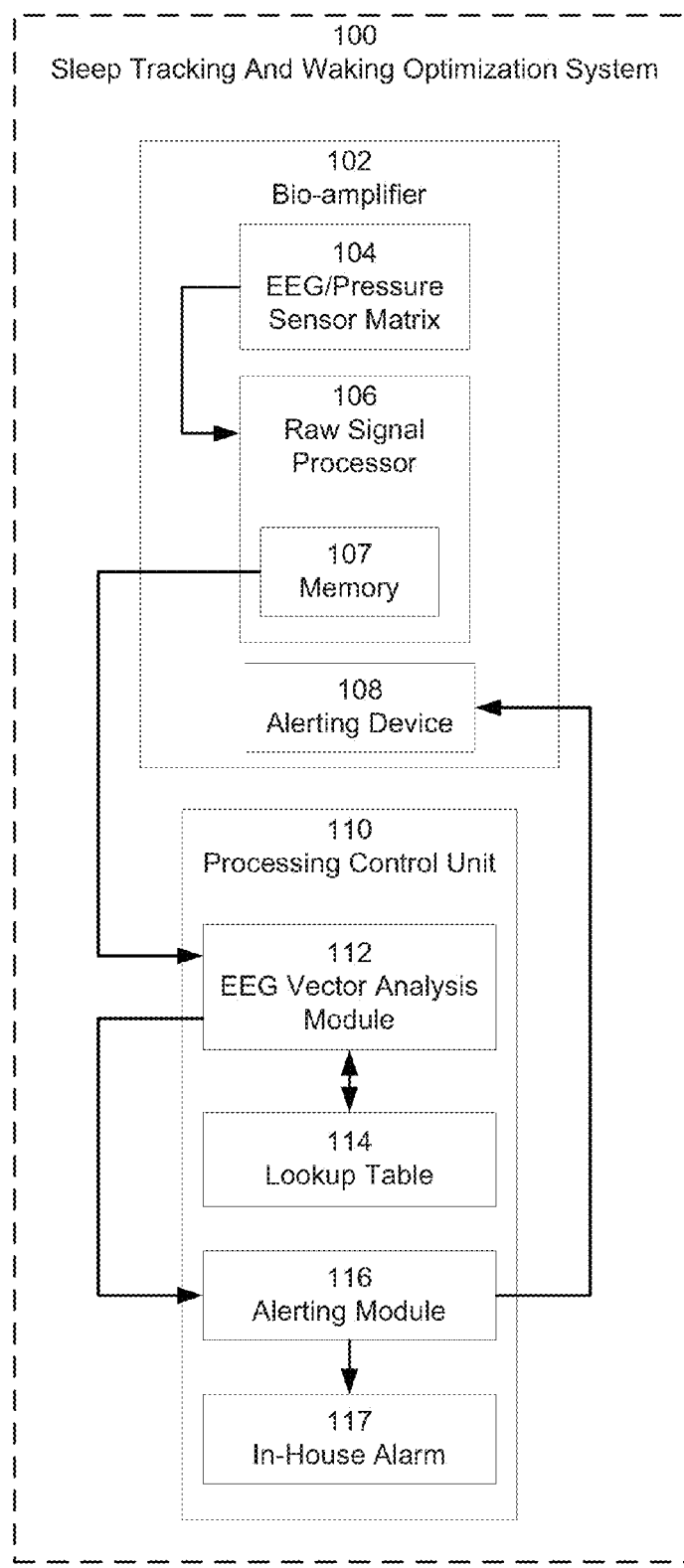
FIG. 1 is a block diagram illustrating a high level view of a sleep tracking and waking optimization system according to an embodiment.

FIG. 1 is a block diagram illustrating a high level view of a sleep tracking and waking optimization system according to an embodiment.

A sleep tracking and waking optimization system 100 includes a bio-amplifier 102, a processing control unit 110 and an alerting module 116. The bio-amplifier 102 includes an EEG/pressure sensor matrix 104, a raw signal processor 106 and an alerting device 108. The alerting device may produce an audio signal or it may vibrate to awaken the subject.

According to an embodiment, the EEG/pressure sensor matrix 104 is a flexible sheet in which both pressure and electrical signal sensors have been embedded. By way of illustration and not by way of limitation, the flexible sheet is embedded on a pillow. As will be explained in more detail below, the EEG/pressure sensor matrix 104 sends analog electrical and pressure data to a raw signal processing module 106 that digitizes the data and stores it in a memory 107.

Figure 2A:
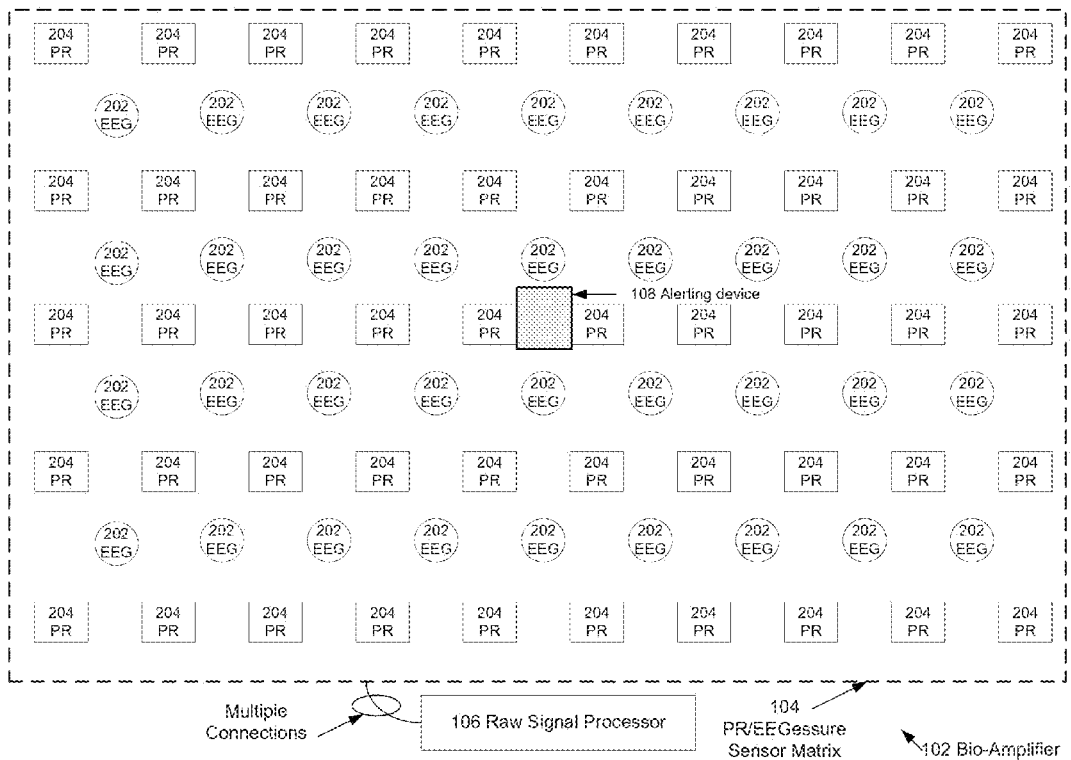
FIG. 2A is a block diagram illustrating a bio-amplifier according to an embodiment.

FIG. 2A is a block diagram illustrating a bio-amplifier according to an embodiment.

In an embodiment, electrodes 202 are placed on a sheet on which the head of a subject under test rests. Contacts between the fabric near an electrode and the subject's head acquire electrical signals from the subject's head. The electrodes 202 feed electrical signals to a raw signal processor 106. Pressure sensors 204 are also embedded in the flexible sheet and acquire pressure data that is used to orient the subject's head as more fully described below.

Figure 2B:
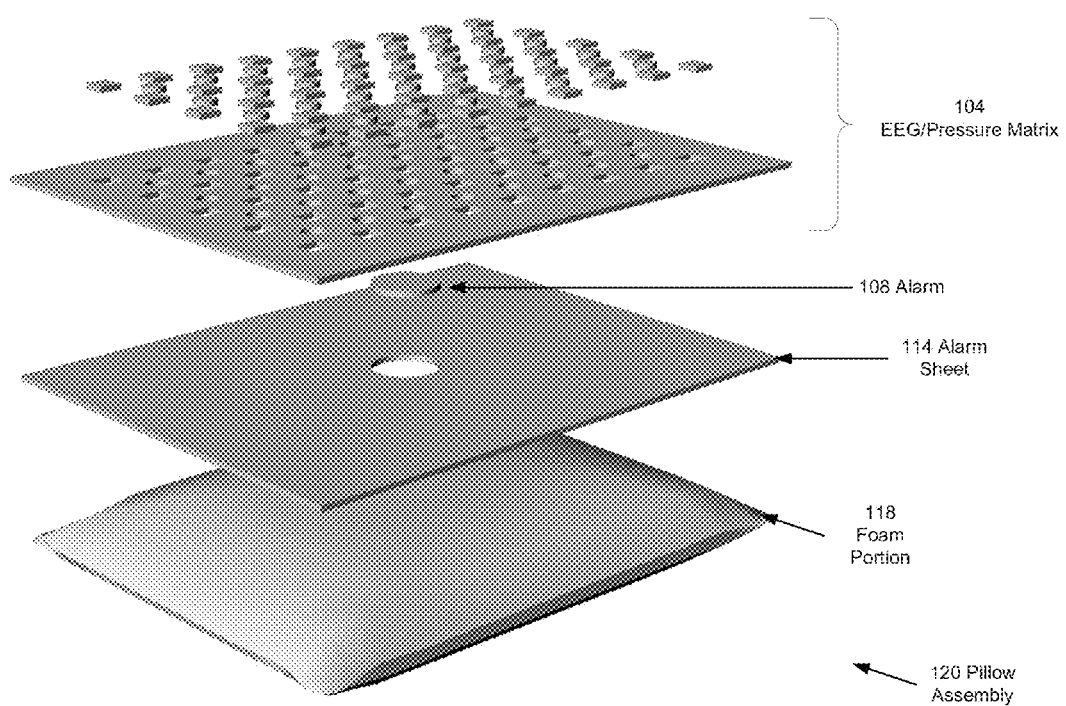
FIG. 2B is an exploded perspective view illustrating components of a pillow assembly incorporating a bio-amplifier according to an embodiment.

FIG. 2B is an exploded perspective view illustrating components of a pillow assembly incorporating a bio-amplifier according to an embodiment. In an embodiment, components of a bio-amplifier 102 are integrated into with a foam portion 118 to form a pillow assembly 120. The pillow assembly 120 may be used in various embodiments described below.

Referring again to FIG. 1, the digitized electrical and pressure data are communicated from the memory 107 to the processing control unit 110. By way of illustration and not by way of limitation, the bio-amplifier may communicate the digitized electrical and pressure data to the processing control unit 110 using a wired or wireless link.

The EEG signal is not acquired from an array of electrodes that are affixed to a subject's head. Rather, the motion of the subject will constantly change the electrode measurement and the reference state of the EEG signal.

FIGS. 3A, 3B and 3C illustrate pressure distributions resulting from three orientations of the head of a subject on pillow incorporating a bio-amplifier 102. In FIG. 3A, the subject's head is flat on the pillow. In this orientation, the pressure is distributed evenly. The pressure gradient is described by a parabolic function orthogonal to the axis of the head defined by the middle of the forehead through the chin. FIGS. 3B and 3C illustrate distribution functions that are not parabolic.

Additionally, the EEG signal is a three-dimensional time-varying vector that measures a mean electrical potential of the brain. A two-dimensional electrical map is not sufficient to map to a three dimensional space.

In an embodiment, pressure is used as an additional variable to create "depth" on the two-dimensional electrode map. The three-dimensional surface defined by pressure is used to solve for the current orientation of the subject's head, as well as for generating a surface to give electrical signals a three-dimensional orientation.

In an embodiment, a pressure surface is defined by the following vector function (where x and y are indices and X and Y are real space):

$$f(x,y) = <X, Y, P> = \vec{P}_{x,y}$$

The following equation is used to obtain the unit normal vector for each electrode (which is given index e).

$$\text{Normal Vector} = \vec{N}_e =$$
$$(\vec{P}_{x+1,y} - \vec{P}_{x,y}) \times (\vec{P}_{x,y+1} - \vec{P}_{x,y}) + (\vec{P}_{x,y} - \vec{P}_{x,y+1}) \times (\vec{P}_{x+1,y+1} - \vec{P}_{x,y+1}) +$$
$$(\vec{P}_{x,y+1} - \vec{P}_{x+1,y}) \times (\vec{P}_{x,y} - \vec{P}_{x+1,y}) +$$
$$(\vec{P}_{x,y+1} - \vec{P}_{x+1,y+1}) \times (\vec{P}_{x+1,y} - \vec{P}_{x+1,y+1})$$

Figure 4A:
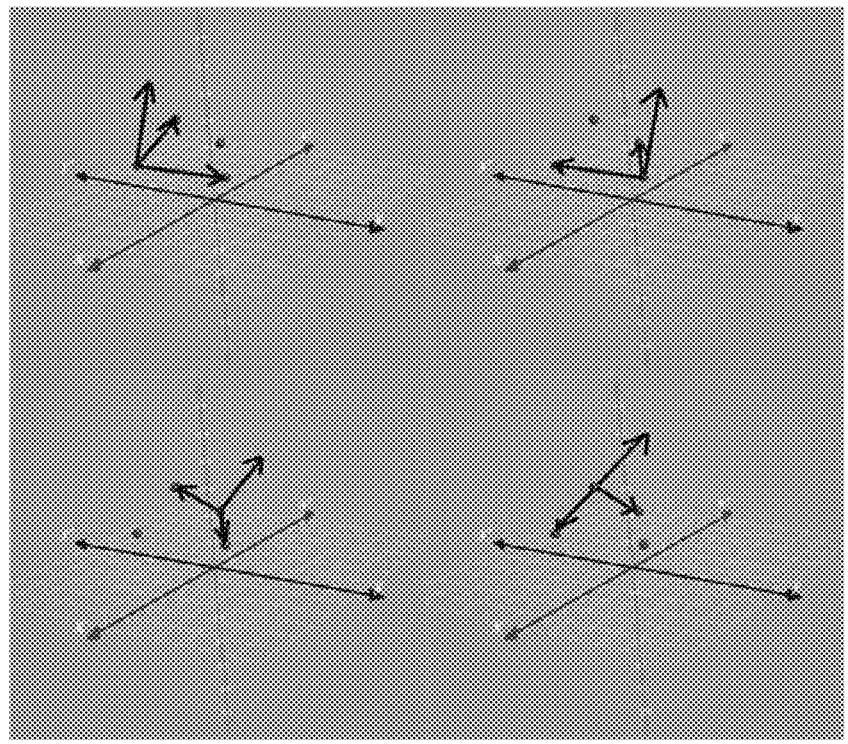
FIG. 4A is a graphical representation illustrating the cross products of the normal vector equation according to an embodiment.

FIG. 4A is a graphical representation illustrating the cross products of the normal vector equation according to an embodiment.

The mean normal vector for the electrode is determined from the following equation:

$$\vec{n}_e = \frac{\vec{N}_e}{|\vec{N}_e|}$$

Figure 4B:
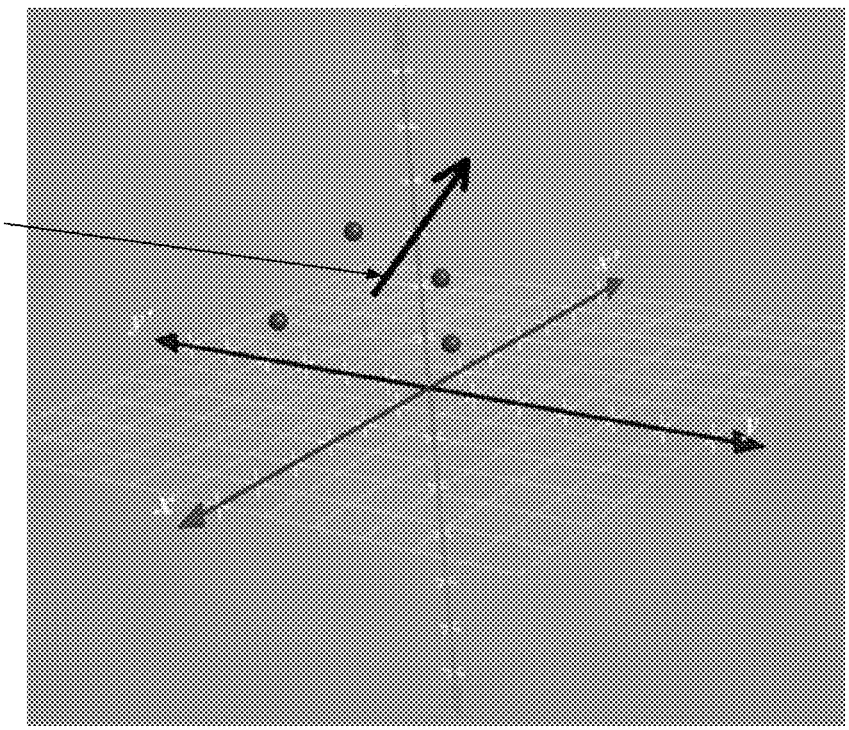
FIG. 4B is a graphical representation illustrating a mean normal vector according to an embodiment.

FIG. 4B is a graphical representation illustrating the mean normal vector 410 according to an embodiment.

Figure 4C:
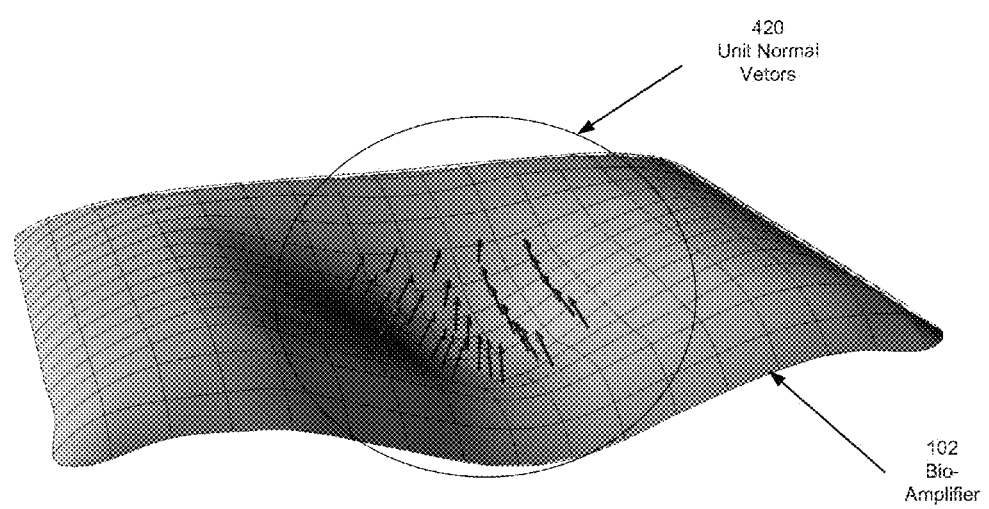
FIG. 4C is a contour drawing illustrating unit normal vectors according to an embodiment.

FIG. 4C is a contour drawing illustrating unit normal vectors 420.

Each electrode is assigned a scalar voltage as follows:

$$V(e) = V_e$$

The relative mean EEG vector is determined as follows:

$$\text{Relative Mean } EEG = \frac{\sum_{e}^{n_e} V_e \vec{n}_e}{n_e}$$

Where $n_e$ is the number of electrodes

When a subject lies on the EEG/pressure sensor matrix 104, a two-dimensional contour map of the pressure on the device is generated. This contour may be represented as the following function:

$$F(x,y) = P$$

Exemplary contours are illustrated in FIGS. 3A, 3B and 3C.

The directional derivative is obtained for the entire vector map in the y direction. All values of y in which the directional derivative passes the $1^{st}$ derivative test for maxima as points $y_{max}$ are obtained, where j is the unit vector in the y direction:

$$\nabla_{\vec{j}} F(x, y) = \frac{\partial P}{\partial y}$$

Solve for $y_{max}$ defined as:

$$\nabla_{\vec{j}} F(x, y_{max}) = 0 \text{ and } \lim_{y \to y_{max}^-} \nabla_{\vec{j}} F(x, y_{max})$$
$$= +0 \text{ and } \lim_{y \to y_{max}^+} \nabla_{\vec{j}} F(x, y_{max})$$
$$= -0$$

There exists a function g such that:

$$g(x) = y_{max}$$

The function g(x) is treated as linear so the rotation θ of the head about the z-axis is defined as:

$$\theta = \tan^{-1}\left(\left\langle \frac{\partial g}{\partial x} \right\rangle_{\text{for all } y_{max}}\right)$$

where $$\left\langle \frac{\partial g}{\partial x} \right\rangle$$

represents the average over a set of point.

All the functions of pressure orthogonal to the linear function g(x) are obtained by reorienting the pressure map and holding the new variables constant.

$$f(a, b) = P \text{ where}$$
$$a = \left\langle \frac{\partial g}{\partial x} \right\rangle_{\text{for all } y_{max}} * x \text{ and } b = \frac{-1}{\left\langle \frac{\partial g}{\partial x} \right\rangle_{\text{for all } y_{max}}} * y$$

If "a" is held constant to $a_0$, a function h of "b" that maps pressure may be obtained:

$$f(a_0, b) = h(b) = P$$

When the head is laying flat on the pillow, regardless of its rotation about the z-axis, it spreads pressure evenly across the pillow. This state may be modeled as a parabola orthogonal to the axis of the head. However, if the head is tilted in either direction, the pressure gradient is no longer parabolic. FIGS. 3B and 3C illustrate distribution functions that are not parabolic.

The difference in pressure growth on both sides of the head can be represented as the $2^{nd}$ derivative of both sides of the pressure map.

The following equation takes the difference of both sides of the pressure curve formed by h(b) and normalizes them to generate a "tilt index":

$$\text{tilt index} = \frac{\left\langle \frac{\partial h}{\partial b} \right\rangle_+ - \left\langle \frac{\partial h}{\partial b} \right\rangle_-}{\left\langle \frac{\partial h}{\partial b} \right\rangle_+ + \left\langle \frac{\partial h}{\partial b} \right\rangle_-}$$

where + and − indicate which side of the parabola the average is taken from.

Table 1 is an illustration of a look-up table that maps measured tilt index values to tilt angles of the head of a subject, based on a sample population deemed representative of typical subjects.

TABLE 1

| Tilt Index | ϕ (tilt angle away from the z-axis) |
|---|---|
| −1.5 | −45 |
| −1 | −30 |
| −.5 | −15 |
| 0 | 0 |
| .5 | 15 |
| 1 | 30 |
| 1.5 | 45 |

In an embodiment, because the function to map tilt index to real head tilt varies significantly from person to person due to head weight, size and shape, a look-up table for a particular subject may be generated by calibrating the pillow for a particular subject. The look up table will then map the tilt index for a given subject to the subject's actual head. See Table 2 for a sample subject's pillow calibration.

TABLE 2

| Calibration | ϕ | Tilt Index |
|---|---|---|
| Head facing up | 0 | 0 |
| Head turned 45° to the left | −45 | −1.56 |
| Head turned 45° to the right | 45 | 1.52 |

After the tilt and rotation are determined, a unit orientation vector in spherical coordinates with rotation θ, tilt Φ and radius of 1 is generated.

This vector is then converted into Cartesian space and then dotted with the relative mean EEG vector to give the absolute scalar EEG signal:

$$\text{Absolute Scalar EEG} = \langle r \sin \Phi \cos \theta, r \sin \Phi \sin \theta, r \cos \Phi \rangle \cdot \text{Relative Mean EEG}$$

This signal is the magnitude projection of the EEG vector onto its correct measurement orientation. This scalar signal is then processed to solve for sleep state.

Referring again to FIG. 1, in an embodiment, the processing control unit 110 includes an EEG vector analysis module 112, a lookup table 114 and an alerting module 116. The processing control unit 110 receives the electrical and pressure data from the raw signal processor and uses a lookup table 114 to derive a correctly oriented EEG mean vector. This vector is computed at fixed intervals to produce an EEG mean vector timeseries.

By way of illustration and not by way of limitation, the processing control unit 110 is incorporated into an alarm clock device, which device also accepts input from the user. In another embodiment, the functions of the processing control unit may be performed by a computing device, such as a computing device illustrated in FIG. 6, executing software instructions. By way of illustration and not by way of limitation, the computing device may be a laptop computer, a desktop computer, or a portable computing device such as a tablet or a smart phone.

The absolute scalar EEG timeseries is provided to the alerting module 116. The alerting module 116 processes the absolute scalar EEG timeseries to determine a sleep state of the subject under test. The alerting module 116 uses the sleep state to issue an alarm signal to an alerting device 108 in the bio-amplifier 102. As further illustrated in FIG. 5 and discussed below, the alerting module may activates an alarm device that is incorporated into a processing control unit or an alarm device that is external to the processing control unit.

In an embodiment, the sleep state of the subject may be mapped over time to determine a sleep cycle pattern. This pattern may be used to project a future sleep state of the subject.

Figure 5:
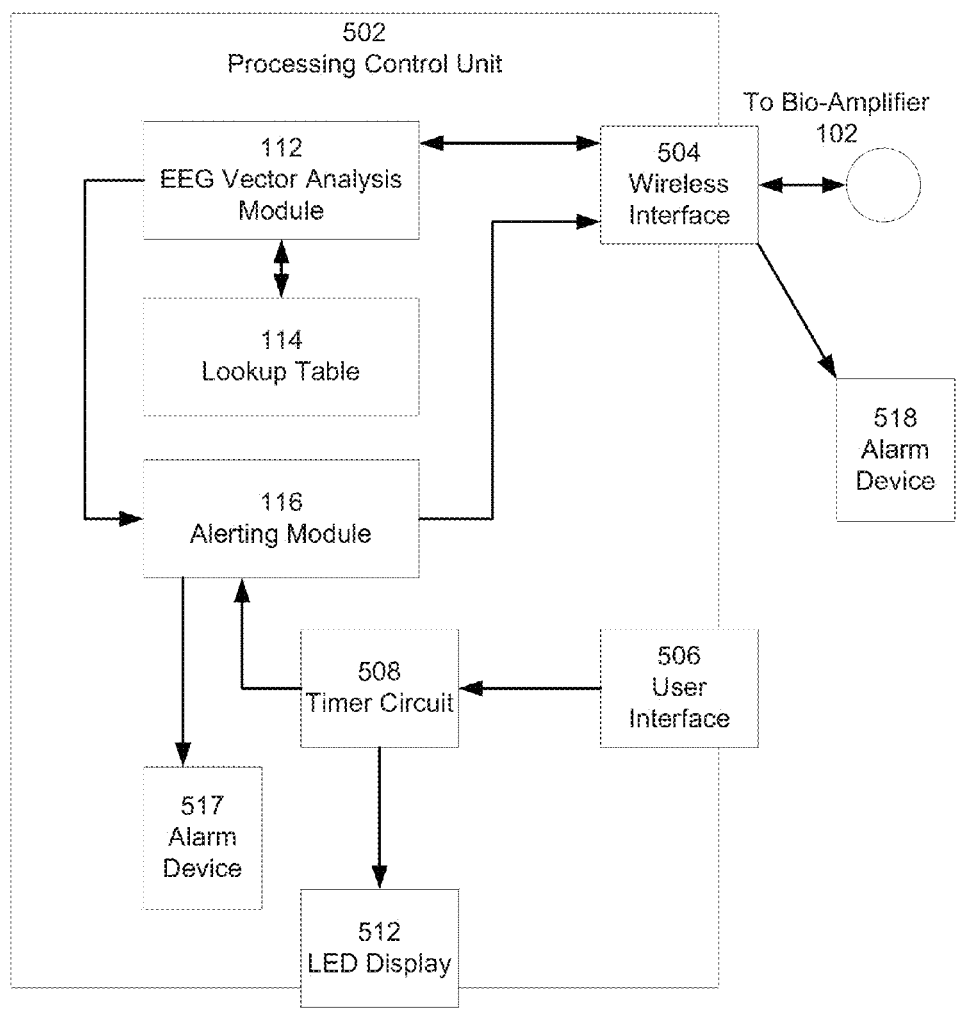
FIG. 5 is a block diagram illustrating a processing control unit according to an embodiment.

FIG. 5 is a block diagram illustrating a processing control unit with added functionality according to an embodiment.

As described above and illustrated in FIG. 1, the processing control unit 110 includes an EEG vector analysis module 112, a lookup table 114 and an alerting module 116. FIG. 5 illustrates a processing control unit 502 that includes additional functional elements that provide user-controllable features. A wireless interface 504 provides communications with the bio-amplifier 102. The wireless interface may be any short-range protocol including, for example, Bluetooth, Wi-Fi, and Zigbee. The processing control unit 502 may receive signal inputs (filtered and amplified EEG and pressure signals) from the memory 107 of the bio-amplifier 102 and may send alarm signals to the alarm 108 and/or an alarm device 517 incorporated into the processing control unit 502 and/or an alarm device 518 that is remote from the processing control unit 502 using the wireless interface 504.

The processing control unit 502 may also include a user interface 506 that receives user selected alarm and timing data. These data are provided to the timer circuit 508 to set a time for display on an LED display device 512. The data may also be used to establish a preferred wake-up time that is provided to the alerting module 116.

In an embodiment, the EEG vector analysis module 112 uses the pressure and EEG data to determine the sleep state of a subject and provides this information to the alerting module 116. The alerting module assesses the trends of the sleep state of the subject against the preferred wake-up time to determine when to activate the alarm 108 component of the bio-amplifier 102. Thus, the activation of the alarm 108 may occur before the preferred wake-up time if needed to optimize the wake time of the subject relative to the subject's sleep state and/or projected sleep state.

Figure 6A:
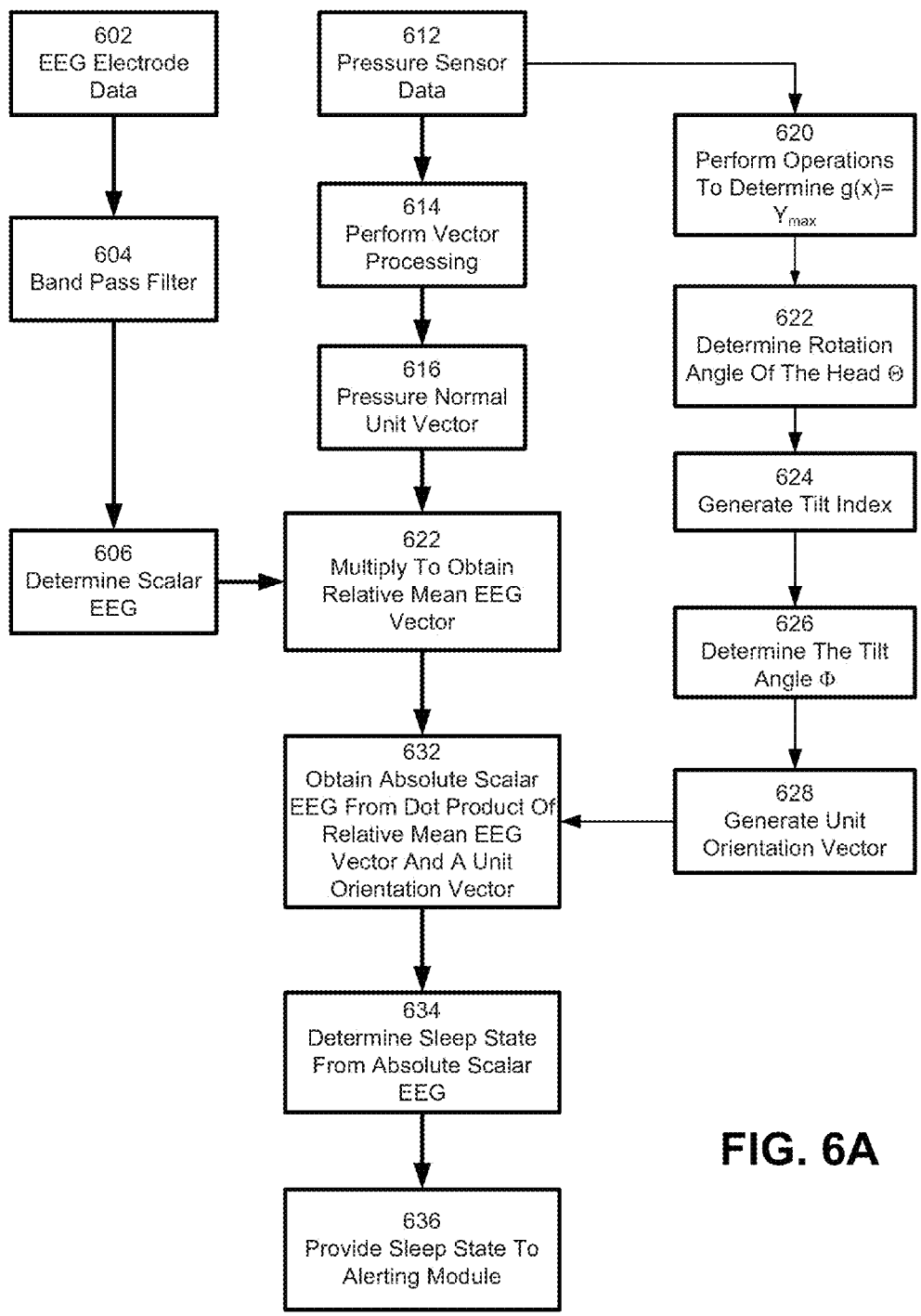
FIG. 6A is a flow diagram illustrating a process by which data from an EEG/pressure sensor matrix is processed according to an embodiment.

FIG. 6A is a flow diagram illustrating a process by which data from an EEG/pressure sensor matrix is processed according to an embodiment.

At Block 602, EEG electrode signals are acquired from the memory 107 of the bio-amplifier 102 (see, FIG. 1). At Block 604 the signals are band passe filtered. At Block 606 a scalar EEG value is obtained. At Block 612 pressure data are acquired from the memory 107 of the bio-amplifier 102 (see, FIG. 1). Vector operations are performed on the pressure data (Block 614) and a pressure normal unit vector is obtained (Block 616).

Operations to determine $g(x)=y_{max}$ are performed a maximum pressure operation (Block 620). The rotation angle of the head $\Theta$ is determined (Block 622). The tilt index is determined (Block 624). The tilt index is used to determine the tilt angle $\Phi$ (Block 626). The pressure normal unit vector is generated (Block 628).

At Block 632, the scalar EEG and pressure normal unit vector are multiplied to obtain a relative mean EEG vector.

At Block 634, an absolute scalar EEG vector is obtained from the dot product of the relative mean EEG vector and a unit orientation vector.

At Block 636, the sleep state of the subject is determined from the absolute scalar EEG vector.

At Block 638, the sleep state is provided to an alerting module.

FIG. 6B is a flow diagram illustrating a process by which a sleep state is identified according to an embodiment.

The EEG signal data from the absolute scalar EEG vector are acquired (Block 632) and converted to a frequency domain using a Fourier transform (Block 634). The amplitude and frequency of the signal is determined (Block 638). Each stage of sleep has its own unique signature of frequencies and amplitudes that identify it. The amplitude and frequency signature of the signal that are obtained by Fourier transforming include real and imaginary components which differ based on the phase shift of the incoming signal.

Figure 6C:
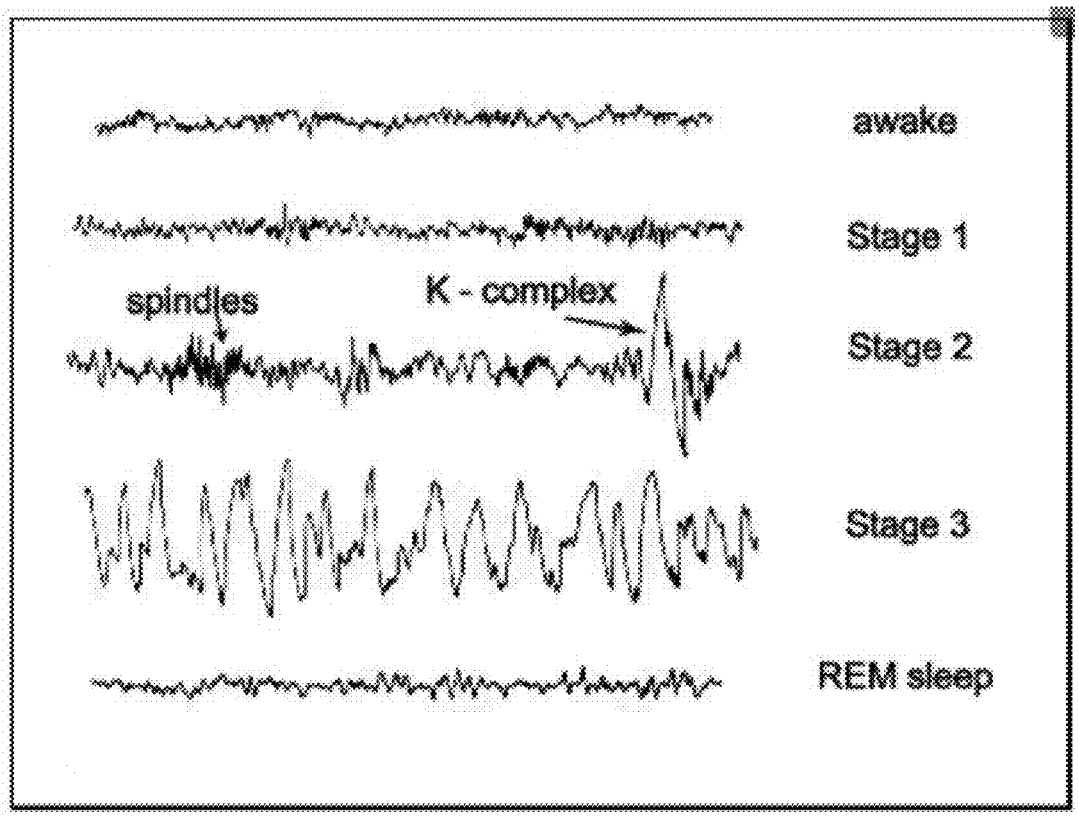
FIG. 6C includes graphs illustrating various sleep state signatures.

FIG. 6C includes graphs illustrating various sleep state signatures. Attributes of the sleep state signatures may be used in at Block 640 to identify a current sleep state of a subject.

Referring again to FIG. 6B, a determination is made at Block 640 whether the data are sufficient to identify the sleep stage of the subject. If the sleep stage cannot be identified from the data, that is, if the result of Block 640 is "NO," the process waits for an updated absolute scalar EEG. In an embodiment, additional data are acquired from the from the memory 107 of the bio-amplifier 102 (see, FIG. 1). In an embodiment, several signal acquisitions may be made and summed to improve the signal to noise ratio. In other embodiment, EEG and pressure data may be recorded for an extended amount of time to mitigate the effects of disturbances to the device and noise.

If the sleep stage can be identified from the data, that is, if the result of Block 640 is "YES," at Block 634 the sleep state is provided the alerting module 116 of the processing control unit 110 (see, FIG. 1). The process continues with additional data being acquired from the memory 107 of the bio-amplifier 102 (see, FIG. 1).

Once an evaluation yields a conclusive result, the algorithm may inform the alerting module of the subject's current sleep stage.

In an embodiment, the process illustrated in FIG. 6A occurs several times each second, and 6B occurs several times each minute, allowing the processing control unit 110 to maintain a strict definition of each stage of sleep. The processing control unit 110 will only alert the alarm component that a change in sleep stage has occurred when it has conclusively made such a determination. Thus, even though the processing control unit 110 may not be able to determine the individual's stage of sleep upon each signal acquisition, it will still report changes in sleep stage with high accuracy.

In an embodiment, when the subject is in a deep sleep and is not projected to be in a light sleep state at a time chosen by the subject to be awakened, the alerting device may be signaled to issue an alarm of a type and/or magnitude that will not awaken the subject but is likely to raise the sleep level of the subject from heavy toward light. The non-awakening alarms may be repeated with varying intensity in order to encourage the subject into a lighter level of sleep. At a point when the subject enters a light level of sleep or the time for awakening have been reached, the alerting device may be signaled to issue an alarm of a type and/or magnitude that will awaken the subject.

Figure 7:
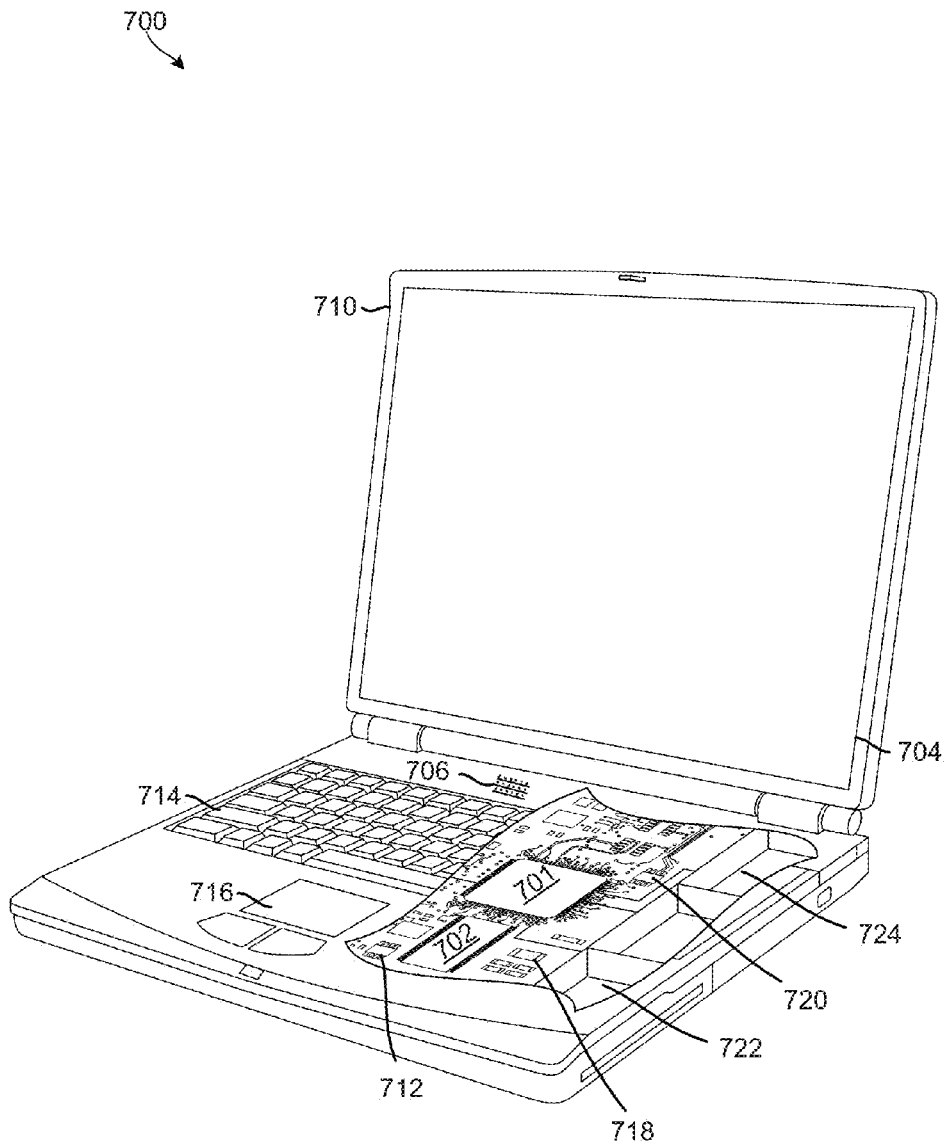
FIG. 7 is a system block diagram of a computing device suitable for use with various embodiments.

FIG. 7 is a system block diagram of a computing device useful to perform functions of a processing control unit. While the computing device 700 is illustrated as a laptop computer, a computing device providing the functional capabilities of the computer device 700 may be implemented as a tablet, a smartphone, a desktop computer or a handheld computer. A typical computing device 700 may include a processor 701 coupled to an electronic display 704, a speaker 706, a volatile memory 702 and to a nonvolatile memory, such as a disk drive 922. When implemented as a laptop computer or desktop computer, the computing device 700 may also include a floppy disc drive, compact disc (CD) or DVD disc drive coupled to the processor 701. The computing device 700 may include an antenna 710, a multimedia receiver 712, a transceiver 718 and/or communications circuitry 920 coupled to the processor 701 for sending and receiving electromagnetic radiation, connecting to a wireless data link, and receiving data from the bio-amplifier 102. Additionally, the computing device 700 may include network access ports 724 coupled to the processor 701 for establishing data connections with a network (e.g., LAN coupled to a service provider network, etc.). A laptop computer or desktop computer 700 typically also includes a keyboard 714 and a mouse pad 716 for receiving user inputs.

It will be understood by those skilled in the art that the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the," is not to be construed as limiting the element to the singular.

What is claimed is:

1. A system for acquiring an EEG signal suitable for use in electroencephalography from a subject, the system comprising:
   a sensor matrix comprising a plurality of EEG electrodes configured to receive electrical signals from the brain of the subject and a plurality of pressure sensors configured to receive pressure signals indicative of the placement of the head of the subject on the sensor matrix;
   a processing control unit configured to perform operations comprising:
      obtaining EEG electrode data from the electrical signals received by the sensor matrix;
      determining a scalar EEG voltage for each EEG electrode;
      obtaining pressure data from the pressure signals received by the sensor matrix;
      determining a pressure normal unit vector for each EEG electrode from the pressure data;
      summing the product of the pressure normal unit vector and the scalar EEG voltage for each EEG electrode to obtain a relative mean EEG vector; and
      obtaining an absolute scalar EEG vector from a dot product of a unit orientation vector and the relative mean EEG vector.

2. The system of claim 1, wherein the sensor matrix comprises a flexible sheet.

3. The system of claim 1, wherein the sensor matrix is a component of a pillow configured for receiving the head of the subject.

4. The system of claim 1, wherein the operation for determining a pressure normal unit vector for each EEG electrode from the pressure signals comprises:
   determining from the pressure data a tilt index indicative of the orientation of the subject's head on the sensor matrix;
   obtaining a tilt angle from the tilt index; and
   obtaining the pressure normal unit vector from the tilt angle.

5. The system of claim 4, wherein the operation of obtaining a tilt angle from the tilt index comprises accessing a look-up table, wherein the look-up table maps tilt index values to tilt angle values.

6. A method for acquiring an EEG signal suitable for use in electroencephalography from a subject, the method comprising:
   receiving by a processor EEG electrode data from a plurality of EEG electrodes residing on a sensor matrix, wherein EEG electrode data are obtained from electrical signals from the brain of the subject;
   determining by the processor a scalar EEG voltage for each EEG electrode;
   receiving by the processor pressure data from a plurality of pressure sensors residing on the sensor matrix, wherein the pressure data are obtained from pressure signals indicative of the placement of the head of the subject on the sensor matrix;
   determining by the processor a pressure normal unit vector for each EEG electrode from the pressure data;
   summing by the processor the product of the pressure normal unit vector and the scalar EEG voltage for each EEG electrode to obtain a relative mean EEG vector; and
   obtaining by the processor an absolute scalar EEG vector from a dot product of a unit orientation vector and the relative mean EEG vector.

7. The method of claim 6, wherein the sensor matrix comprises a flexible sheet.

8. The method of claim 6, wherein the sensor matrix is a component of a pillow configured for receiving the head of the subject.

9. The method of claim 6, wherein determining a pressure normal unit vector for each EEG electrode from the pressure signals comprises:
   determining from the pressure data a tilt index indicative of the orientation of the subject's head on the sensor matrix;
   obtaining a tilt angle from the tilt index; and
   obtaining the pressure normal unit vector from the tilt angle.

10. The method of claim 9, wherein obtaining a tilt angle from the tilt index comprises accessing a look-up table, wherein the look-up table maps tilt index values to tilt angle values.

11. A system for awakening a subject, the system comprising:
   a pillow comprising:
      a sensor matrix, wherein the sensor matrix comprises a plurality of EEG electrodes configured to receive electrical signals from the brain of the subject and a plurality of pressure sensors configured to receive pressure signals indicative of the placement of the head of the subject on the sensor matrix;
      a memory for receiving EEG electrode data derived from the electrical signals and receiving pressure data derived from the pressure signals; and
      an alerting device; and
   a processing control unit configured to perform operations comprising:
      obtaining the EEG electrode data from the memory;

determining a scalar EEG voltage for each EEG electrode;

obtaining pressure data from the memory;

determining a pressure normal unit vector for each EEG electrode from the pressure data;

summing the product of the pressure normal unit vector and the scalar EEG voltage for each EEG electrode to obtain a relative mean EEG vector;

obtaining an absolute scalar EEG vector from a dot product of a unit orientation vector and the relative mean EEG vector;

determining a sleep state of the subject from the absolute scalar EEG vector; and issuing a command to power on the alerting device to awaken the subject while the subject is in or is approaching a light sleep state.

12. The system of claim 11, wherein the sensor matrix comprises a flexible sheet.

13. The system of claim 11, wherein the operation for determining a pressure normal unit vector for each EEG electrode from the pressure signals comprises:

determining from the pressure data a tilt index indicative of the orientation of the subject's head on the sensor matrix;

obtaining a tilt angle from the tilt index; and obtaining the pressure normal unit vector from the tilt angle.

14. The system of claim 13, wherein the operation of obtaining a tilt angle from the tilt index comprises accessing a look-up table, wherein the look-up table maps tilt index values to tilt angle values.

15. The system of claim 11, wherein the pillow and the processing control unit are connected to a wireless network and the operations of obtaining EEG electrode data, obtaining pressure data, and issuing a command to power on the alerting device are performed over a wireless network.

16. The system of claim 11, wherein the processing control unit further comprises a user interface and a timer circuit and wherein the processing control unit is configured to perform operations comprising:

receiving via the user interface a wake-up time from the subject; and issuing the command to the alerting device to awaken the subject while the subject is in or is approaching a light sleep state at or about the wake-up time.

17. The system of claim 11, wherein the processing control unit is configured to perform operations comprising:

determining that the subject will not enter a light sleep state at or about the wake-up time;

issuing a first command to the alerting device to power on the alerting device at first level selected to modify a current sleep state to a light sleep state without awakening the subject;

determining a new sleep state;

issuing a second command to the alerting device to power on the alerting device at a second level selected to modify the new sleep state to a light sleep state without awakening the subject when the new sleep state is not a light sleep state; and issuing the command to the alerting device to awaken the subject at or about the wake-up time when the subject is in or is approaching a light sleep state after the first or second commands.

18. The system of claim 11, wherein the alerting device is selected from the group consisting of an alarm that vibrates, an alarm that issues an audible signal alarm and an alarm that vibrates and issues a audible signal.

19. The system of claim 11, wherein the operations performed by the processing control unit are performed by a computing device selected from the group consisting of a laptop computer, a desktop computer, a portable computing device, a tablet and a smart phone.

20. A method for awakening a subject, the method comprising:

receiving by a processor EEG electrode data from a plurality of EEG electrodes residing on a sensor matrix, wherein EEG electrode data are obtained from electrical signals from the brain of the subject;

determining by the processor a scalar EEG voltage for each EEG electrode;

receiving by the processor pressure data from a plurality of pressure sensors residing on the sensor matrix, wherein the pressure data are obtained from pressure signals indicative of the placement of the head of the subject on the sensor matrix;

determining by the processor a pressure normal unit vector for each EEG electrode from the pressure data;

summing by the processor the product of the pressure normal unit vector and the scalar EEG voltage for each EEG electrode to obtain a relative mean EEG vector; and obtaining by the processor an absolute scalar EEG vector from a dot product of a unit orientation vector and the relative mean EEG vector determining a sleep state of the subject from the absolute scalar EEG vector; and issuing a command to power on an alerting device to awaken the subject while the subject is in or is approaching a light sleep state.

21. The method of claim 20, wherein the sensor matrix comprises a flexible sheet.

22. The method of claim 20, wherein the sensor matrix is a component of a pillow configured for receiving the head of the subject.

23. The method of claim 20, wherein determining a pressure normal unit vector for each EEG electrode from the pressure signals comprises:

determining from the pressure data a tilt index indicative of the orientation of the subject's head on the sensor matrix;

obtaining a tilt angle from the tilt index; and obtaining the pressure normal unit vector from the tilt angle.

24. The method of claim 23, wherein obtaining a tilt angle from the tilt index comprises accessing a look-up table, wherein the look-up table maps tilt index values to tilt angle values.

25. The method of claim 20, wherein the steps of obtaining pressure data, and issuing a command to power on the alerting device are performed over a wireless network.

26. The method of claim 20 further comprising:

receiving via a user interface a wake-up time from the subject; and issuing the command to the alerting device to awaken the subject while the subject is in or is approaching a light sleep state at or about the wake-up time.

27. The method of claim 26 further comprising:

determining that the subject will not enter a light sleep state at or about the wake-up time;

issuing a first command to the alerting device to power on the alerting device at first level selected to modify a current sleep state to a light sleep state without awakening the subject;

determining a new sleep state;

issuing a second command to the alerting device to power on the alerting device at a second level selected to modify the new sleep state to a light sleep state without awakening the subject when the new sleep state is not a light sleep state; and issuing the command to the alerting device to awaken the subject at or about the wake-up time when the subject is in or is approaching a light sleep state after the first or second commands.

28. The method of claim 20, wherein the alerting device is selected from the group consisting of an alarm that vibrates, an alarm that issues an audible signal alarm and an alarm that vibrates and issues an audible signal.

29. The method of claim 20, wherein the processor is a component of a computing device selected from the group consisting of a laptop computer, a desktop computer, a portable computing device, a tablet and a smart phone.

\* \* \* \* \*